United States Patent
Lin et al.

(10) Patent No.: US 9,521,964 B2
(45) Date of Patent: Dec. 20, 2016

(54) SYSTEM AND METHOD FOR ESTIMATING THE MECHANICAL BEHAVIOR OF HUMAN LOWER LIMBS

(75) Inventors: Shih-Yun Lin, Tainan (TW); Chi-Kang Wu, Taipei (TW); Chih-Hung Huang, Tainan (TW); Chueh-Shan Liu, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 850 days.

(21) Appl. No.: 13/563,694

(22) Filed: Jul. 31, 2012

(65) Prior Publication Data
US 2013/0165820 A1 Jun. 27, 2013

(30) Foreign Application Priority Data
Dec. 23, 2011 (TW) .............................. 100148303 A

(51) Int. Cl.
| | | |
|---|---|---|
| A61B 5/103 | (2006.01) | |
| A61B 5/117 | (2016.01) | |
| A61B 5/107 | (2006.01) | |
| A61B 5/00 | (2006.01) | |

(52) U.S. Cl.
CPC ........... *A61B 5/1038* (2013.01); *A61B 5/1074* (2013.01); *A61B 5/6807* (2013.01); *A61B 5/6829* (2013.01); *A61B 2562/04* (2013.01)

(58) Field of Classification Search
CPC ... A61B 5/1038; A61B 5/6807; A61B 5/1074; A61B 5/6829; A61B 2562/04
USPC ................................................. 600/587–595
See application file for complete search history.

(56) References Cited

U.S. PATENT DOCUMENTS

| | | | |
|---|---|---|---|
| 4,813,436 A | 3/1989 | Au | |
| 6,183,425 B1 * | 2/2001 | Whalen et al. | 600/592 |
| 6,360,597 B1 * | 3/2002 | Hubbard, Jr. | 73/172 |
| 2005/0010139 A1 | 1/2005 | Aminian et al. | |

(Continued)

FOREIGN PATENT DOCUMENTS

| | | |
|---|---|---|
| CN | 101524196 | 9/2009 |
| JP | 2009106391 | 5/2009 |

(Continued)

OTHER PUBLICATIONS

Mueller et al., "Differences in the Gait Characteristics of Patients With Diabetes and Peripheral Neuropathy Compared With Age-Matched Controls", Journal of the American Physical Therapy Association 74 (4), Apr. 1994, p. 299-p. 308.

(Continued)

*Primary Examiner* — Max Hindenburg
*Assistant Examiner* — Jonathan M Foreman
(74) *Attorney, Agent, or Firm* — Jianq Chyun IP Office

(57) ABSTRACT

A system and a method for estimating the mechanical behavior of human lower limbs is provided. The method includes the following steps: sensing a plurality of foot pressure signals of a user by using a sensor array, the foot pressure signals comprising at least a rearfoot pressure signal and at least a forefoot pressure signal; calculating a temporal sequence of a gait cycle of the user according to the foot pressure signals; calculating a foot reaction force of the user according to the foot pressure signals and a calibration parameter; and calculating a mechanical state of the lower limb joints of the user according to the temporal sequence of the gait cycle and the foot reaction force.

9 Claims, 5 Drawing Sheets

(56) References Cited

U.S. PATENT DOCUMENTS

| | | |
|---|---|---|
| 2008/0216593 A1 | 9/2008 | Jacobsen et al. |
| 2009/0137933 A1 | 5/2009 | Lieberman et al. |
| 2010/0152629 A1 | 6/2010 | Haas, Jr. et al. |
| 2011/0054358 A1 | 3/2011 | Kim et al. |
| 2011/0146396 A1 | 6/2011 | Kim et al. |
| 2012/0035509 A1* | 2/2012 | Wilson et al. ............... 600/592 |

FOREIGN PATENT DOCUMENTS

| | | |
|---|---|---|
| TW | 201114408 | 5/2011 |
| WO | 9514430 | 6/1995 |
| WO | 2005094679 | 10/2005 |
| WO | 2008111800 | 9/2008 |

OTHER PUBLICATIONS

"Office Action of Taiwan counterpart application" issued on Oct. 21, 2013, p. 1-p. 10.

Fong et al., "A three-pressure-sensor (3PS) system for monitoring ankle supination torque during sport motions", Journal of Biomechanics, May 2008, vol. 41, p. 2562-p. 2566.

Liu et al., "Lower extremity joint torque predicted by using artificial neural network during vertical jump", Journal of Biomechanics, Jan. 2009, vol. 42, p. 906-p. 911.

Forner Cordero et al., "Use of pressure insoles to calculate the complete ground reaction forces", Journal of Biomechanics, Dec. 2003, vol. 37, p. 1427-p. 1432.

Forner-Cordero et al., "Inverse dynamics calculations during gait with restricted ground reaction force information from pressure insoles", Gait & Posture, Feb. 2005, vol. 23, p. 189-p. 199.

Gage, "Basic Measurement Techniques", Gait Analysis in Cerebral Palsy, Oct. 1991, p. 12-p. 36.

* cited by examiner

SYSTEM AND METHOD FOR ESTIMATING THE MECHANICAL BEHAVIOR OF HUMAN LOWER LIMBS

CROSS-REFERENCE TO RELATED APPLICATION

This application claims the priority benefit of Taiwan application serial no. 100148303, filed on Dec. 23, 2011. The entirety of the above-mentioned patent application is hereby incorporated by reference herein and made a part of this specification.

TECHNICAL FIELD

This disclosure relates to human biomechanics, including a system and a method for estimating the mechanical behavior of human lower limbs.

BACKGROUND

With changes in lifestyle and an aging population, people are paying more attention to their health and spending more time exercising, and the market for sporting goods and fitness equipment has prospered. Lots of new types of equipment have been introduced. The treadmill, which encompasses 30 percent of the entire fitness equipment market, has become accepted by most people for its simple and regular exercise pattern. The treadmill is also popular for its effectiveness in training the muscle strength of the lower limbs and increasing cardiopulmonary endurance.

The commercial treadmill is typically equipped with a compact digital display that can only provide basic parameters like exercise time, exercise distance, mechanical resistance, mechanical rotation speed, or energy consumption. Due to a lack of information, the user does not receive dynamic information from the lower limbs while running on this kind of treadmill, and the risk of injuries from overuse or overexertion increases dramatically when the user exercises in an abnormal posture. Only a few costly treadmills, such as the Compact Tandem Force-Sensing Treadmill produced by AMTI Co. or the Fully Instrumented Treadmill produced by Bertec Co., can calculate the force and moment around the user's limbs and joints or output the temporal-spatial parameters during exercise. These treadmills are usually used for research.

Although commercial fitness equipment manufacturers realize that dynamic information is crucial for the user, the problems associated with component configuration and signal acquisition render it impossible for them to install sensor components like load sensor, force plate, strain gauge or pressure sensor into the equipment. Moreover, hurdles in signal integration and transmission need to be overcome. Only a few manufacturers with enough resources and capability are qualified to make high quality fitness equipment and the market is restricted by its high price and low consumer acceptance.

SUMMARY

An exemplary embodiment of the disclosure provides a system for estimating mechanical behavior of human lower limbs, including an input module, a sensor array, a calculation module, and an output module. The input module is configured to input and record a data of the user. The sensor array is configured to sense a plurality of foot pressure signals of the user. The sensor array includes at least a first sensor and at least a second sensor, in which the first sensor is disposed on a rearfoot of the user, and the second sensor is disposed on a forefoot of the user. The calculation module is coupled to the input module, and the calculation module is configured to calculate a temporal sequence of a gait cycle, a foot reaction force, and a mechanical state of the lower limb joints of the user according to the user foot pressure signals. The output module is coupled to the calculation module, and the output module is configured to output or display the temporal sequence of the gait cycle, the foot reaction force, or the mechanical state of the lower limb joints of the user.

Another exemplary embodiment of the disclosure provides a method for estimating mechanical behavior of the human lower limbs. The method includes: sensing a plurality of foot pressure signals of a user by using a sensor array, the foot pressure signals comprising at least a rearfoot pressure signal and at least a forefoot pressure signal; calculating a temporal sequence of a gait cycle of the user according to the foot pressure signals; calculating a foot reaction force of the user according to the foot pressure signals and a calibration parameter; and calculating a mechanical state of the lower limb joints of the user according to the temporal sequence of the gait cycle and the foot reaction force.

Several exemplary embodiments accompanied with figures are described in detail below to further describe the disclosure in detail.

BRIEF DESCRIPTION OF THE DRAWINGS

The accompanying drawings constituting a part of this specification are incorporated herein to provide a further understanding of the disclosure. Here, the drawings illustrate embodiments of the disclosure and, together with the description, serve to explain the principles of the disclosure.

DESCRIPTION OF EMBODIMENTS

Figure 1:
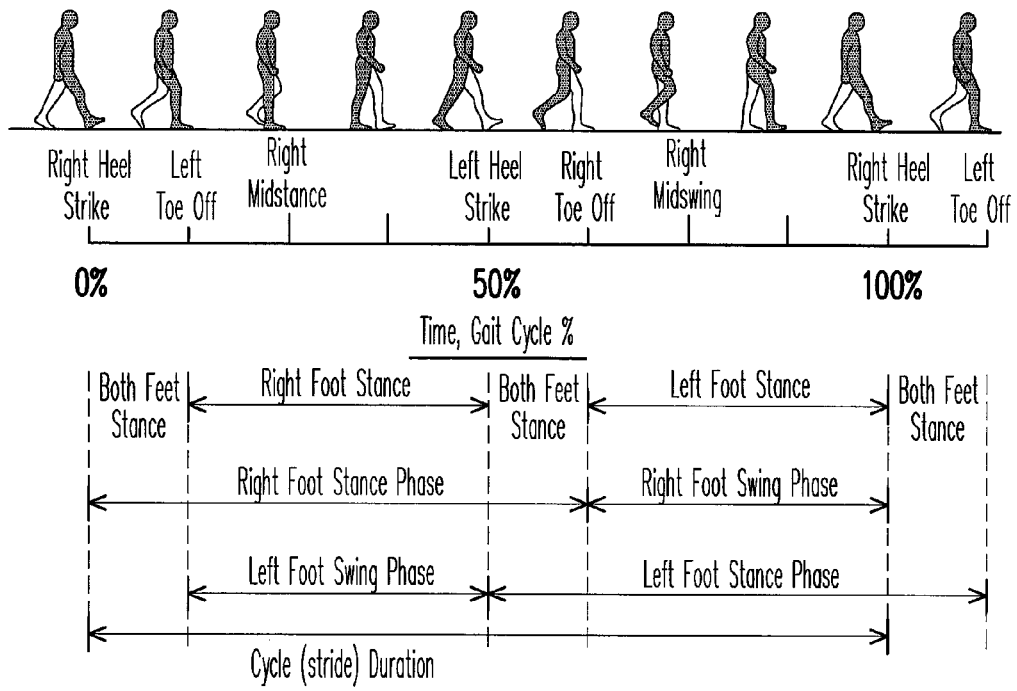
FIG. 1 is a schematic view of a normal temporal-spatial cyclic property of a human gait motion according to an exemplary embodiment.

Reference will now be made in detail to the present embodiments of the disclosure, examples of which are illustrated in the accompanying figures. Moreover, elements/ components/notations with the same reference numerals represent the same or similar parts in the drawings and embodiments.

FIG. 1 is a schematic view of a normal temporal-spatial cyclic property of a human gait motion according to an exemplary embodiment. With reference to FIG. 1, one normalized cycle time is set to be 100%. Taking a right foot, depicted by gray in the example, and starting from 0% of the gait cycle. The stance phase is defined as that 60% of the gait cycle during which the right heel is in contact with the ground, up until the right toe is lifted off the ground. The swing phase is defined as that 40% of the time of the gait cycle during which the right foot is entirely off the ground. A similar situation exists for the left foot. Moreover, both feet of a normal person are illustrated in FIG. 1, and both the left foot gait and the right foot have a stance phase and a swing phase.

Normally, the human gait has a fixed temporal-spatial cyclic property, and the body weight forms a center of pressure (COP) on the foot sole. Therefore, as long as the gait motion is in a normal condition, the COP generates a fixed COP progression pathway 201 in accordance with a temporal sequence of the gait cycle (as shown in FIG. 2A).

Figures 2A, 2B:
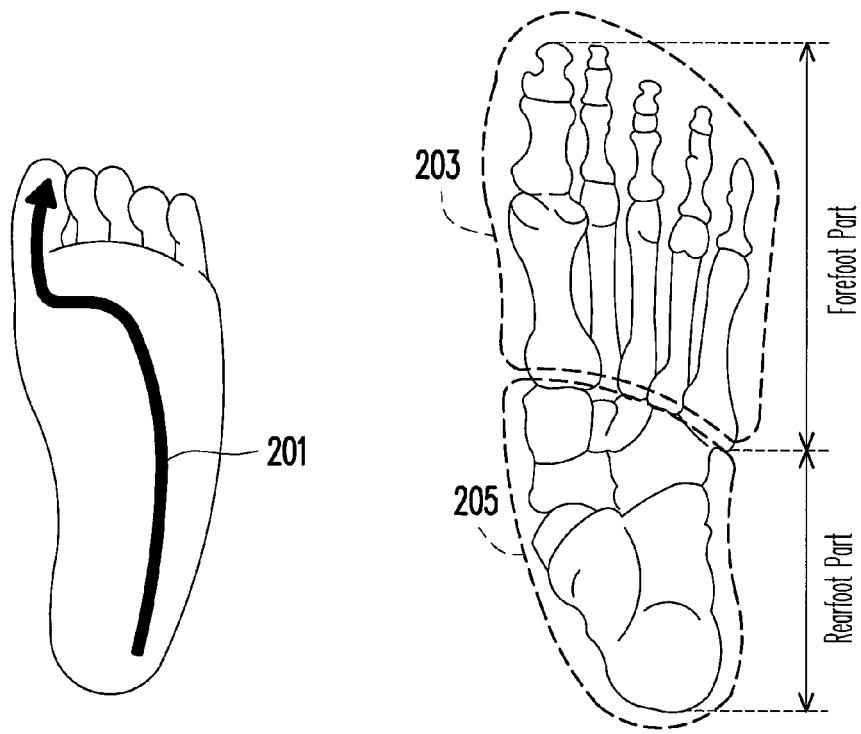
FIG. 2A is a schematic view of a center of foot pressure progression pathway according to an exemplary embodiment.
FIG. 2B is a schematic view of a forefoot part and a rearfoot part of a foot.

FIG. 2B is a schematic view of a forefoot part and a rearfoot part of a foot. Each normal foot has five toes and a heel. A forefoot part 203 may be defined as a front half region including the five toes and the metatarsal bones. A rearfoot part 205 may be defined as a back half region including the heel. Similarly, footwear such as shoes, socks, specialized sneakers, or protective gears encompassing the foot, may also be divided into the forefoot part and the rearfoot part according to different locations of the foot. When the human body carries out the gait motion, the direction of the COP progression pathway 201 is from the rearfoot part 205 towards the forefoot part 203.

Figure 3A:
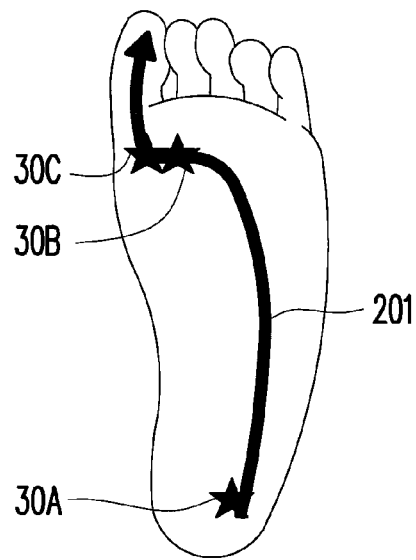
FIG. 3A is a schematic distribution view of the regions of pressure concentration of a foot.
Figure 3B:
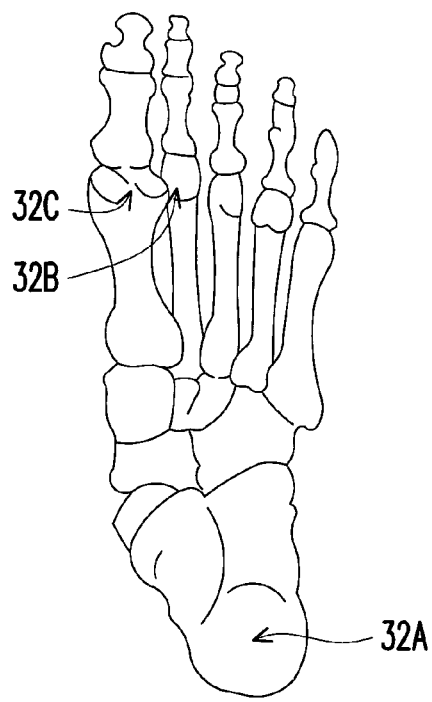
FIG. 3B is a positional diagram of the regions of pressure concentration of a foot relative to the skeletal regions in anatomy.

FIG. 3A is a schematic distribution view of the regions of pressure concentration of a foot. FIG. 3B is a positional diagram of the regions of pressure concentration of a foot relative to skeletal regions in anatomy. By actually measuring, several regions of pressure concentration on the foot COP progression pathway 201 are displayed obviously, and these regions are located at a rearfoot part 30A and the forefoot part 30B and 30C. Generally speaking, each metatarsal bone has two ends. One end farther away from the heart is referred as a distal end, and the other end closer to the heart is referred as a proximal end. In the present embodiment, the location of the rearfoot part 30A is below the foot calcaneus bone 32A of the foot. The locations of the forefoot part 30B and 30C are below the distal end 32B of the second metatarsal bone, and below the distal end 32C of the first metatarsal bone, respectively.

Figure 4:
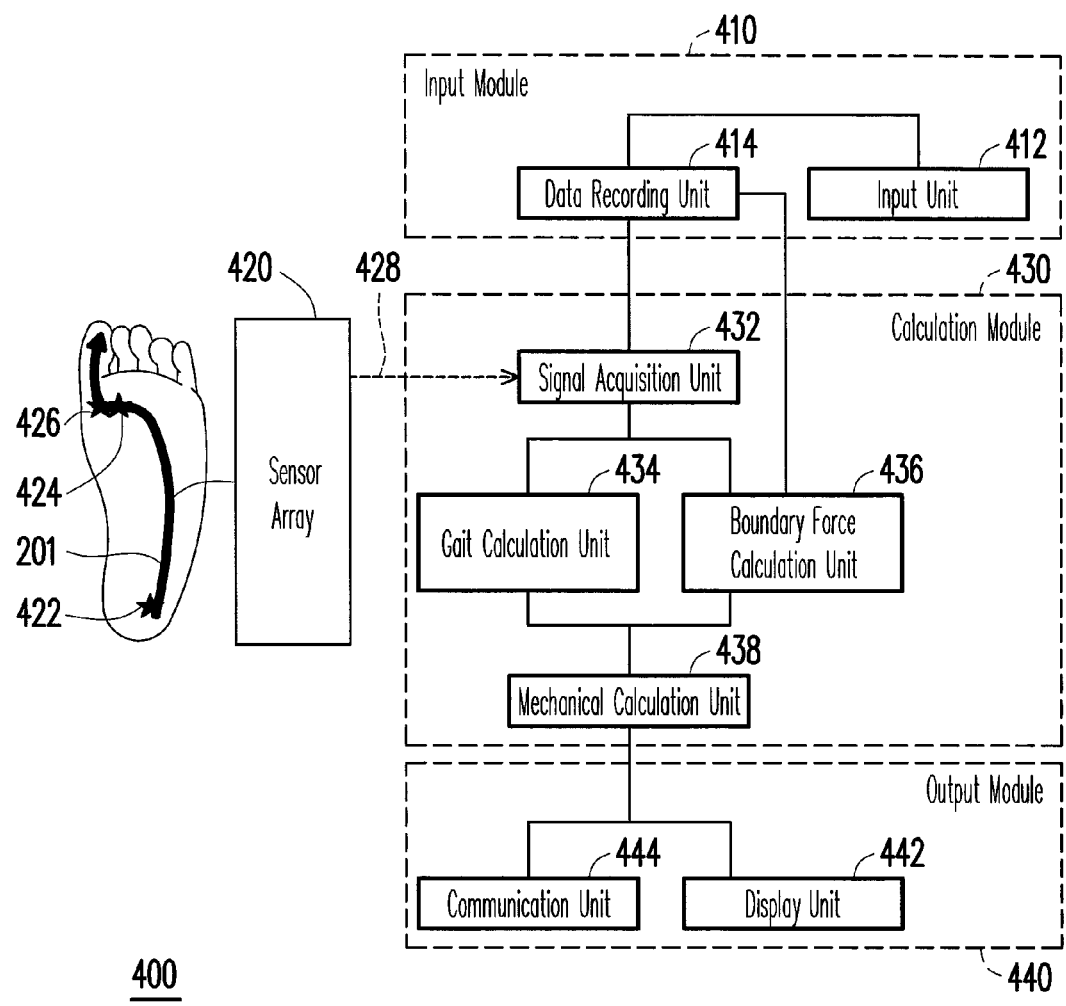
FIG. 4 is a block diagram of a system for estimating the mechanical behavior of human lower limbs according to an exemplary embodiment.

FIG. 4 is a block diagram of a system for estimating the mechanical behavior of the human lower limbs according to an exemplary embodiment. With reference to FIG. 4, an estimation system 400 includes an input module 410, a sensor array 420, a calculation module 430, and an output module 440.

The input module 410 is configured to input and record basic data of the user. The input module 410 may include an input unit 412 and a data recording unit 414. The input unit 412 serves as an interface for the user to input the basic data. The data recording unit 414 may be configured to record a height, a body weight, an age, a gender, or a race of the user.

The sensor array 420 may be applied on footwear such as shoes, socks, specialized sneakers, or protective gears encompassing the foot. For sensing a plurality of foot pressure signals 428 of the user, the sensor array 420 is disposed on the footwear on the foot COP progression pathway 201 matching a human gait. The sensor array 420 includes a plurality of sensors 422-426. The sensor 422 is disposed on the rearfoot part of the footwear for sensing a rearfoot pressure signal below the foot calcaneus bone. The sensor 424 is disposed on the footwear below the distal end of the second metatarsul bone relative to the foot, and the sensor 424 is configured to sense a forefoot pressure signal on the footwear. The sensor 426 is disposed on the footwear below the distal end of the first metatarsul bone relative to the foot, and the sensor 426 is configured to sense another forefoot pressure signal on the footwear. It should be noted that, the placement of the sensors needs to be on the foot COP progression pathway 201 matching the human gait, and the number of the sensors is not limited by the embodiment.

The sensors in the sensor array 420 may be resistive pressure sensors or capacitive pressure sensors. A wire may be used to connect between each of the sensors in the sensor array 420. In addition, a wire or a wireless communication connection may be used to connect between the sensor array 420 and the calculation module 430.

In the present embodiment, the calculation module 430 is coupled to the input module 410. The calculation module 430 is configured to calculate a temporal sequence of a gait cycle, a foot reaction force, and a mechanical state of the lower limb joints of the user according to the basic data and the foot pressure signals 428 of the user. The temporal sequence of the gait cycle refers to the repeated and fixed time progression properties of a human gait motion. The gait motion may be divided into a plurality of phases, including a heel strike phase, a foot flat phase, a midstance phase, a toe off phase, and a midswing phase. Therefore, each phase of the gait motion may be correspondingly represented by a percentage value, and the temporal sequence of the gait cycle may correspond to the foot pressure signals. The mechanical state of the lower limb joints includes a moment exerted from the muscle groups around the joints, a compression force endured by the hip joint, a compression force endured by the knee joint, a tension force endured by the connective tissue around the ankle joint, a tension force endured by the connective tissue around the knee joint, or a tension force endured by the connective tissue around the hip joint.

In the present embodiment, the details of the calculation module 430 includes a signal acquisition unit 432, a gait calculation unit 434, a boundary force calculation unit 436, and a mechanical calculation unit 438. The signal acquisition unit 432 is coupled to the data recording unit 414. The gait calculation unit 434 is coupled to the signal acquisition unit 432, and the boundary force calculation unit 436 is coupled to the signal acquisition unit 432 and the data recording unit 414. The mechanical calculation unit 438 is coupled to the gait calculation unit 434 and the boundary force calculation unit 436.

Figure 5:
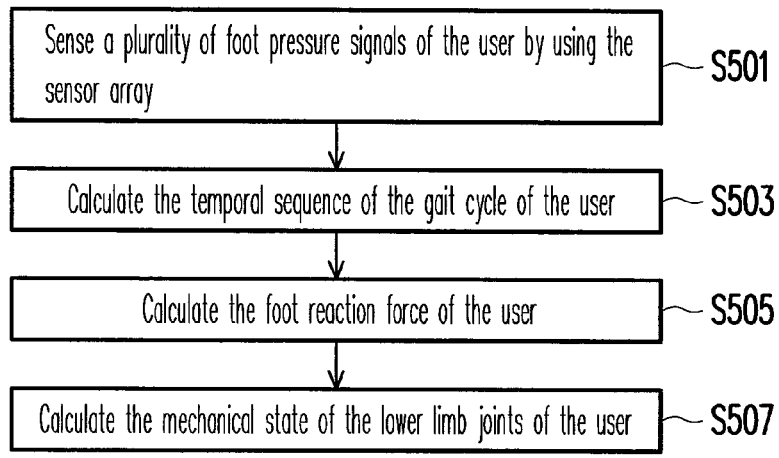
FIG. 5 is a flow chart of a method for estimating the mechanical behavior of human lower limbs according to an exemplary embodiment.

The following procedure is the method of the calculation module 430 to calculate the mechanical behavior of human lower limbs. FIG. 5 is a flow chart of a method for estimating the mechanical behavior of human lower limbs according to an exemplary embodiment. Please refer to FIGS. 4 and 5.

As shown in a Step S501, a plurality of foot pressure signals 428 of the user are sensed by using the sensor array 420. The foot pressure signals 428 include at least one rearfoot pressure signal and at least one forefoot pressure signal. In the present embodiment, there are two forefoot pressure signals, although the disclosure is not limited thereto.

In a Step S503, the calculation unit 434 calculates the temporal sequence of the gait cycle of the user according to the foot pressure signals 428. The signal acquisition unit 432 acquires the foot pressure signals 428 by a wired method or a wireless method, and outputs the foot pressure signals 428 to the gait calculation unit 434. Moreover, the foot pressure signals 428 may be converted and recorded in the data recording unit 414 of the input module 410. The gait calculation unit 434 calculates the temporal sequence of the gait cycle according to an appearance sequence or a relative strength ratio of the foot pressure signals 428. For example, the gait calculation unit 434 determines a starting point of a gait cycle (0% of gait cycle) according to an appearance of a foot pressure signal of the sensor 422. When the foot pressure signals on the sensors 424 and 426 have disappeared, it represents the toes are off the ground (60% of gait cycle) and may be used as an end point to determine the stance phase. Moreover, the temporal order of the human gait motion is calculated through the temporal-spatial variations of the foot pressure signals 428.

In a Step S505, the boundary force calculation unit 436 calculates the foot reaction force of the user according to the foot pressure signals 428 and a calibration parameter. The generation method of the calibration parameter is described later in the disclosure.

In a Step S507, the mechanical calculation unit 438 calculates the mechanical state of the lower limb joints of the user according to the temporal sequence and the foot reaction force of the gait cycle obtained above. The mechanical state of the lower limb joints includes the moment exerted from the muscle groups around the joints, the compression force endured by the hip joint, the compression force endured by the knee joint, the tension force endured by the connective tissue around the ankle joint, the tension force endured by the connective tissue around the knee joint, or the tension force endured by the connective tissue around the hip joint.

Moreover, the temporal sequence of the gait cycle, the foot reaction force, and the mechanical state of the lower limb joints of the user obtained by the calculation module 430 may be displayed or outputted through the coupled output module 440. For example, in FIG. 4 the output module 440 includes a display unit 442. In one embodiment, the display unit 442 may be configured to display the temporal sequence of the gait cycle, the foot reaction force, and the mechanical state of the lower limb joints of the user. In another embodiment, the output module 440 includes a communication unit 444 configured to provide a communication function to connect with a monitor device or an external device, such as a watch, a cell phone, a personal digital assistant (PDA), a tablet computer (e.g. iPad), or portable or wearable electronic devices. Accordingly, the output module 440 may be configured to output the temporal sequence of the gait cycle, the foot reaction force, and the mechanical state of the lower limb joints of the user to the external device, and every mechanical behavior value of the human lower limb can be displayed by the external device. The communication unit 444 may be a radio frequency transceiver, a Bluetooth transceiver, or a ZigBee wireless communication unit, although the disclosure is not limited thereto.

According to the description of the various embodiments above, the sensor array (e.g. a plurality of pressure sensors) may be disposed on footwear frequently use in daily life, and the sensor array can be used to measure the pressure signals of the foot during the human gait motion. Moreover, according to the known and fixed temporal-spatial cyclic property corresponding to the human gait motion, the temporal sequence of the gait cycle can be calculated through the temporally related pressure signals which are measured by the sensor array. The temporal sequence is the temporal-spatial parameters of the human gait motion. Finally, the mechanical values endured by the lower limbs or joints may be derived according to the temporal sequence of the gait cycle and the foot reaction force. Moreover, the calculated data may be transmitted to the external device, such as to the electronic device of the user including a smartphone, a personal computer, a sports watch, or transmitted to the electronic display device of the sporting equipment.

Figure 6:
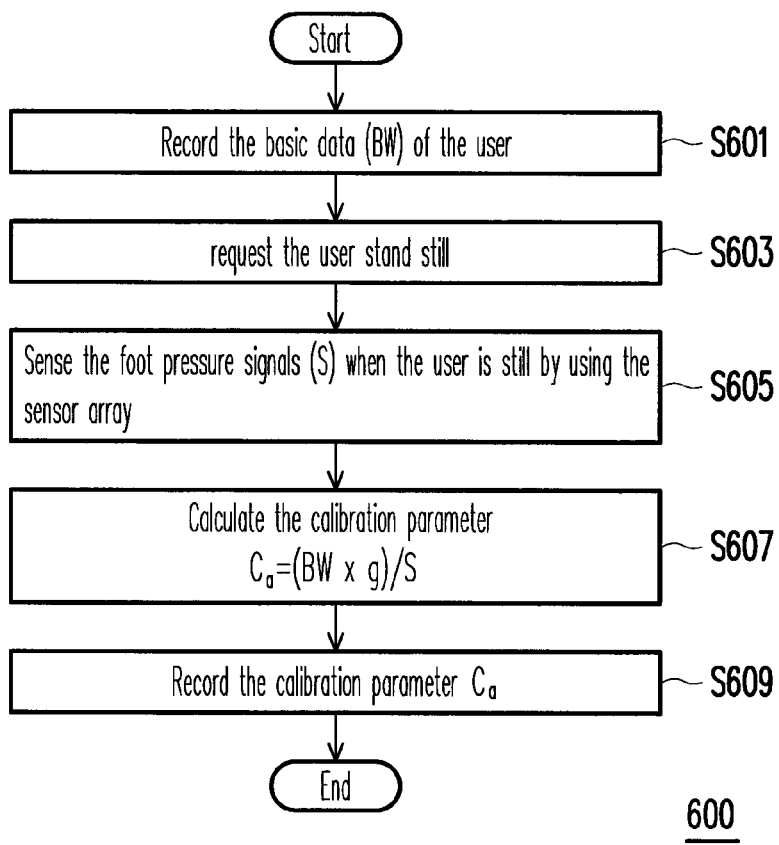
FIG. 6 is a flow chart of a calibration parameter generating process according to an exemplary embodiment.

Next, the method to generate the calibration parameter is described as follows. FIG. 6 is a flow chart of a calibration parameter generating process 600 according to an exemplary embodiment. The present embodiment further elaborates on the details of generating the calibration parameter.

In a Step S601, the basic data of the user is recorded. The basic data may be a height, a body weight, an age, a gender, or a race of the user, for example. In a Step S603, the user is requested to keep a static posture and stand for a period of time. Moreover, in a Step S605, the sensor array is used to sense the foot pressure signals when the user is stand still.

Next, in a Step S607, the calibration parameter calculation is executed. A calibration parameter $C_a$ may be obtained by dividing a known gravity value of a body weight force BW×g by a total value S of the foot pressure signals. BW is a human body weight value, and the units of BW is kilogram (kg). g is a gravitational constant, and the value of g is approximately 9.81 under the meter-kilogram-second (MKS) system. The value of the foot pressure signal is typically a voltage value in units of volt (V). After completing the Step S607, the calibration parameter $C_a$ is recorded in a Step S609. The calibration parameter $C_a$ may be configured to estimate the foot reaction force of the user in the gait motion.

Figure 7:
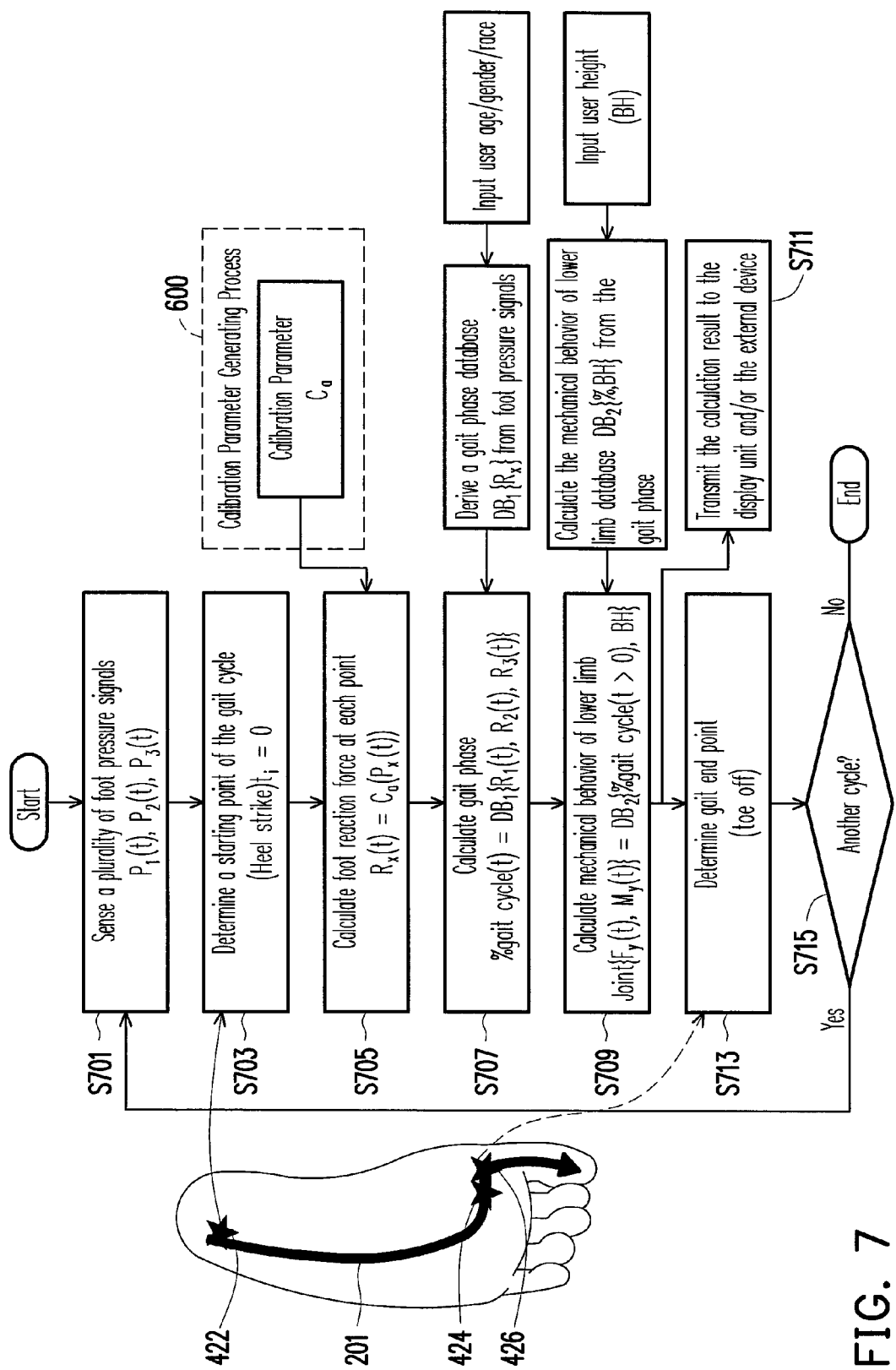
FIG. 7 is a flow chart of an analytical process of the mechanical behavior of human lower limbs according to an exemplary embodiment.

Another embodiment is described hereafter to elaborate on an analytical process of the mechanical behavior of human lower limb. Please refer to FIG. 7. In order to description clearly, the sensor array is disposed on the footwear on the foot COP progression pathway 201 matching the human gait. The sensor array 420 including sensors 422-426 are configured to sense a plurality of foot pressure signals of the user. The number of the sensors is not limited thereto.

As shown in a Step S701, a plurality of foot pressure signals $P_1(t)$, $P_2(t)$, and $P_3(t)$ related to the temporal domain are sensed by using the sensor array 420. $P_1$, $P_2$, and $P_3$ are the signals sensed by the sensors 422, 424, and 426, respectively, and (t) represents a time-related function.

As shown in a Step S703, a starting point of the gait cycle is defined by determining a signal sensed by the sensor 422 disposed at a heel part. The starting point occurs at a time of a heel strike signal, and the time of the gait starting point is defined as $t_i=0$.

Thereafter, as shown in a Step S705, by using the calibration parameter $C_a$ obtained from the completed calibration parameter generating process 600, a foot reaction force endured by the foot is calculated with a $C_a$ function. The foot reaction force $R_x(t)=C_a(P_x(t))$, in which x=1, 2 or 3.

As shown in a Step S707, a gait phase percentage % gait cycle(t)=$DB_1\{R_1(t), R_2(t), R_3(t)\}$ of the gait cycle is calculated, so as to calculate the temporal sequence of the gait cycle according to an appearance sequence of the foot pressure signals $P_1(t)$, $P_2(t)$, and $P_3(t)$ or a relative strength ratio of this signals. Moreover, $DB_1$ represents a gait phase database function derived from the foot pressure signals of a specific group, and the function is calculated by the appearance sequence of the foot pressure signals $P_1(t)$, $P_2(t)$, and $P_3(t)$ and the relative strength ratio of the signals $P_1(t)$, $P_2(t)$, and $P_3(t)$. This specific group is defined by the user's age, gender, and race.

As shown in a Step S709, the mechanical behavior of the lower limbs is calculated by using the gait phase and the reaction force. The estimation may be completed by referencing the gait temporal sequence and the joint force database in gait motion and multiplying by a lower limb instantaneous reaction force. In one embodiment of the calculation, a mechanical state of the lower limb joints Joint$\{F_y(t), M_y(t)\}$=DB$_2$\{% gait cycle(t>0), BH\} of the user may be calculated, in which $F_y(t)$ represents a function related to the strength of the force, $M_y(t)$ represents a function related to the moment, and DB$_2$ represents a function related to the database of mechanical behavior of the lower limbs calculated from the same described specific group by using the gait phase. The function DB$_2$ uses the gait phase to deduce the mechanical behavior performance of the lower limbs, and the function takes a user height (BH) as an input to serve as a reference condition for correcting the lower limb mechanical deduction value.

As shown in a Step S711, after completing the Step S709, an instantaneous lower limb gait phase and the mechanical information are transmitted to the display unit and/or the external device for data display.

Thereafter, as shown in a Step S713, after completing the Step S709, the end point of the gait cycle may be determined when the foot pressure signals of the forefoot part have disappeared, representing that the toes are off the ground.

In the analytical process of the mechanical behavior of human lower limbs according to the present exemplary embodiment, as shown in a Step S715, when another gait cycle has been determined to exist, the Steps S701 to S715 are repeated until the gait cycle is terminated.

Moreover, in another embodiment, after calculating the lower limb mechanical state of the user in Step S709, the differences between the mechanical state of the lower limb joints and a known human normal state may be further compared, so as to transmit a warning signal to the user when divergence from the human normal state occurs. The known human normal state here refers to a state obtained by sensing under no external injuries or special illnesses.

According to the foregoing exemplary embodiments, not only can the sensor array be disposed on footwear such as shoes, socks, specialized sneakers, or protective gears encompassing the foot for sensing the foot pressure signals, but these signals may be stored temporally, and used to calculate the temporal sequence of the human gait and the mechanical state of the lower limb joints. Moreover, besides knowing the amount of compression force endured by the ankle from the mechanical state of the lower limb joints, the moment exerted from the muscle groups around the thigh or the lower leg can be known when the user is running or walking. Alternatively, the joint mechanical state of one segment or more can also be known, for example the moment exerted from the muscle groups around the joints, or the compression force endured by the hip joint, the compression force endured by the knee joint, the tension force endured by the connective tissue around the ankle joint, the tension force endured by the connective tissue around the knee joint, or the tension force endured by the connective tissue around the hip joint.

In view of the foregoing, since the system and method for estimating mechanical behavior of human lower limbs according to the disclosure can sense the foot pressure signals by disposing the sensor array on the center of foot pressure progression pathway matching the human gait. Not only the temporal sequence of the gait cycle and the foot reaction force of the user can be calculated, but the joint mechanical state of one segment or more can also be calculated. On the other hand, conventionally the user can only learn the mechanical information endured by the limbs in the laboratory. In this disclosure, the sensor array employs simple components to overcome limitations of environment and materials, and the real-time monitoring is available for the user to reduce the injuries from exercise.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A system for estimating the mechanical behavior of human lower limbs, comprising:
    an input module, configured to input and record a data of a user;
    a sensor array, comprising no more than a first sensor, a second sensor and a third sensor, each of the first, second and third sensors being positioned along a foot center of pressure (COP) progression pathway, disposed on a first and/or second region of a support surface of an object to sense a plurality of foot pressure signals of the user, wherein the first region and the second region are respectively disposed at two opposite ends on a same side of the support surface of the object;
    a calculation module coupled to the input module, configured to calculate a temporal sequence of a gait cycle, a foot reaction force, and a mechanical state of the lower limb joints of the user by an appearance sequence of the foot pressure signals or a relative strength ratio of the foot pressure signals according to the data of the user and the foot pressure signals of the user; and
    an output module coupled to the calculation module, configured to output the temporal sequence of the gait cycle, the foot reaction force, or the mechanical state of the lower limb joints of the user.

2. The system for estimating the mechanical behavior of human lower limbs as claimed in claim 1, wherein the mechanical state of the lower limb joints comprises a moment exerted from the muscle groups around the joints, a compression force endured by the hip joint, a compression force endured by the knee joint, a tension force endured by the connective tissue around the ankle joint, a tension force endured by the connective tissue around the knee joint, or a tension force endured by the connective tissue around the hip joint.

3. The system for estimating the mechanical behavior of human lower limbs as claimed in claim 1, wherein the input module comprises:
    a data recording unit, configured to record a height, a body weight, an age, a gender, or a race of the user.

4. The system for estimating the mechanical behavior of human lower limbs as claimed in claim 1, wherein the first, second and third sensors are resistive pressure sensors or capacitive pressure sensors.

5. The system for estimating the mechanical behavior of human lower limbs as claimed in claim 1, wherein the output module comprises:
    a communication unit, configured to provide a communication function to connect with an external device.

6. The system for estimating the mechanical behavior of human lower limbs as claimed in claim 5, wherein the communication unit is a radio frequency transceiver, a Bluetooth transceiver, or a ZigBee wireless communication unit.

7. The system for estimating the mechanical behavior of human lower limbs as claimed in claim 1, wherein a wire or a wireless communication connection is configured to connect between the sensor array and the calculation module.

8. The system for estimating the mechanical behavior of human lower limbs as claimed in claim 1, wherein the calculation module comprises:

a signal acquisition unit coupled to the input module, configured to acquire the foot pressure signals, and record the foot pressure signals in the input module;

a gait calculation unit coupled to the signal acquisition unit, configured to calculate the temporal sequence of the gait cycle according to the appearance sequence or the relative strength ratio of the foot pressure signals;

a boundary force calculation unit coupled to the signal acquisition unit, configured to calculate the foot reaction force according to the foot pressure signals and a calibration parameter; and a mechanical calculation unit coupled to the gait calculation unit and the boundary force calculation unit, configured to calculate the mechanical state of the lower limb joints according to the temporal sequence of the gait cycle and the foot reaction force.

9. The system for estimating the mechanical behavior of human lower limbs as claimed in claim 8, wherein the gait calculation unit determines a starting point of the gait cycle according to whether a foot pressure signal of the first and second sensors appear, and calculates the temporal sequence of the gait cycle through the foot pressure signals.

* * * * *